United States Patent

Kawachi et al.

Patent Number: 5,892,118
Date of Patent: Apr. 6, 1999

[54] PROCESS FOR PRODUCING 4,6-DIAMINORESORCINOLS

[75] Inventors: Junji Kawachi; Hironori Matsubara; Yoshinori Nakahara, all of Wakayama; Yutaka Watanabe, Matsuyama, all of Japan

[73] Assignee: Daiwa Kasei Industry Co., Ltd., Wakayama, Japan

[21] Appl. No.: 947,160

[22] Filed: Oct. 8, 1997

[30] Foreign Application Priority Data

Oct. 9, 1996 [JP] Japan .................... 8-353834

[51] Int. Cl.⁶ .................... C07C 215/78; C07C 209/58
[52] U.S. Cl. .................... 564/443; 564/414
[58] Field of Search .................... 564/414, 443, 564/158, 159

[56] References Cited

U.S. PATENT DOCUMENTS

| | | | |
|---|---|---|---|
| 3,901,925 | 8/1975 | Devlin et al. | 260/345.3 |
| 4,302,599 | 11/1981 | Peer et al. | 564/146 |
| 4,705,896 | 11/1987 | Van Der Puy et al. | 564/265 |
| 5,254,684 | 10/1993 | Izumi et al. | 564/215 |
| 5,679,865 | 10/1997 | Hoefnagel et al. | 568/319 |

FOREIGN PATENT DOCUMENTS

H07-316102  12/1995  Japan .

*Primary Examiner*—Shailendra Kumar
*Attorney, Agent, or Firm*—Armstrong, Westerman, Hattori, McLeland & Naughton

[57] ABSTRACT

A process for producing 4,6-diaminoresorcinols comprises the steps of:

subjecting a dioxime of the formula (4)

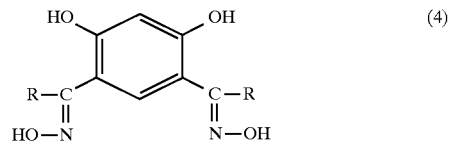

wherein R is an alkyl or phenyl group, to Beckmann rearrangement to thereby produce 4,6-diacylaminoresorcinol of the formula (5)

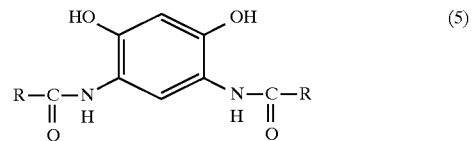

wherein R is as defined above, and subjecting the 4,6-diacylaminoresorcinol to hydrolysis and recovering the product 4,6-diaminoresorcinol (6)

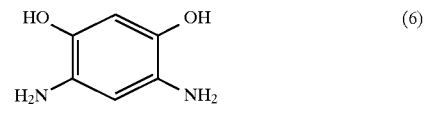

or a salt thereof.

7 Claims, No Drawings

PROCESS FOR PRODUCING 4,6-DIAMINORESORCINOLS

FIELD OF THE INVENTION

The present invention relates to an industrially advantageous process for producing 4,6-diaminoresorcinols which are useful as starting materials for polybenzobisoxazole resins.

DESCRIPTION OF THE PRIOR ART

Polybenzobisoxazole resins are excellent in such properties as heat resistance, chemical resistance, strength and elasticity. They are produced by using 4,6-diaminoresorcinol or a salt thereof as a starting monomer. Processes for producing 4,6-diaminoresorcinol or a salt thereof are known as follows.

A first process comprises nitrating resorcinol diacetate and then reducing the nitration product to give 4,6-diaminoresorcinol. Refer to, for example, "Macromolecules, 14, 909 (1981)". This process may be represented by the following formula (a):

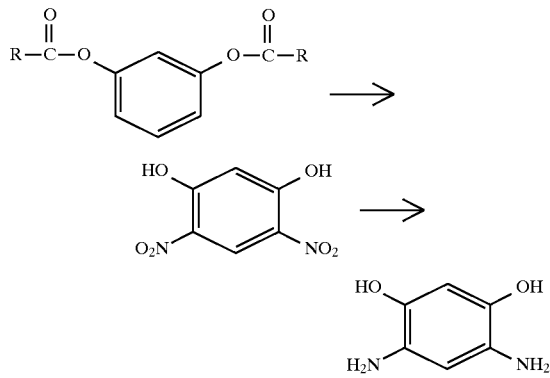

A second process comprises nitrating a 1,3-dihalobenzene or 1,2,3-trihalobenzene and hydrolyzing the resulting 1,3-dihalo-4,6-dinitrobenzene or 1,2,3-trihalo-4,6-dinitrobenzene with an alkali, followed by reduction to give 4,6-diaminoresorcinol. Refer to, for example, Japanese Kokai Tokkyo Koho H01-238561. This process may be represented by the following formula (b):

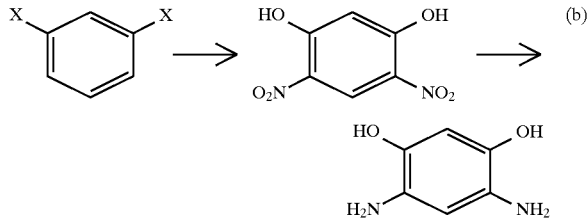

wherein X represents halogen.

According to a modification of said second process as disclosed in Japanese Kokai Tokkyo Koho H07-316102, a 1,3-disubstituted-4,6-dinitrophenol is first prepared from a 1,3-dihalo-4,6-dinitrobenzene and it is then hydrolyzed to give 4,6-dinitroresorcinol. Reduction of this 4,6-dinitroresorcinol gives 4,6-diaminoresorcinol.

The above-mentioned first process for producing 4,6-diaminoresorcinol has its drawbacks in that the desired intermediate 4,6-dinitroresorcinol has to be separated and purified from the mixture of mono-, di- and trinitro compounds produced by nitration and, in addition, the yield is low. The byproduct trinitro compound is explosive, hence dangerous in handling.

The above-mentioned second process for producing 4,6-diaminoresorcinol allows nitro group introduction into positions 4 and 6 with relatively high regioselectivity. However, 4,6-dinitroresorcinol is unstable under alkaline conditions and the alkaline hydrolysis generally gives low yields. The modification, according to Japanese Kokai Tokkyo Koho H07-316102, of said second process has a problem in that the operational procedure is complicated.

Thus, the known processes which use a nitro compound or a halogen compound as an intermediate each has various problems from the industrial process viewpoint, namely problems from the viewpoint of regioselectivity of nitration, toxicity, danger, severe reaction conditions in alkali hydrolysis step, site selectivity in relation to amino and hydroxy groups, and so forth.

With such prior art in the background, it is an object of the present invention to provide an industrially advantageous process for producing 4,6-diaminoresorcinols which involves no nitro or halogen compound, gives high regioselectivity in substituent introduction and can give the desired product in high yields.

SUMMARY OF THE INVENTION

The process for producing 4,6-diaminoresorcinol according to the present invention comprises subjecting a dioxime of the formula (4)

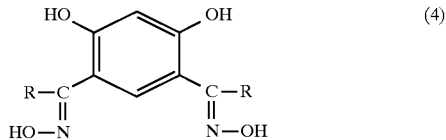

wherein R is an alkyl or phenyl group, to Beckmann rearrangement, then subjecting the resulting 4,6-diacylaminoresorcinol of the formula (5)

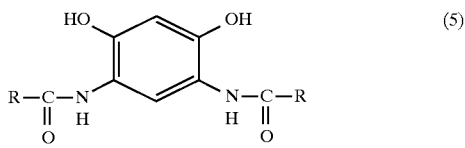

wherein R is as defined above, to hydrolysis, and recovering 4,6-diaminoresorcinol of the formula (6)

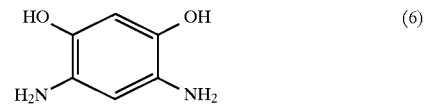

or a salt thereof.

DETAILED DESCRIPTION OF THE INVENTION

Steps A to E

The steps for obtaining 4,6-diaminoresorcinol according to the present invention are as follows.

Step A: The step of acylating resorcinol to give an diacylated compound;

Step B: The step of subjecting the diacylated compound to Fries rearrangement to give a 4,6-diacylresorcinol;

Step C: The step of oximating the 4,6-diacylresorcinol to give the corresponding dioxime;

Step D: The step of subjecting the dioxime to Beckmann rearrangement to give the corresponding 4,6-diacylaminoresorcinol;

Step E: The step of hydrolyzing the 4,6-diacylaminoresorcinol to give 4,6-diaminoresorcinol or a salt thereof.

Of the above steps, steps D and E are the essential constituents of the present invention. Steps A to C are typical steps for preparing the dioxime to be used in step D. For facilitating understanding, the steps from step A are described step by step in the following.

Step A

Step A is the step of acylating resorcinol of the formula (1)

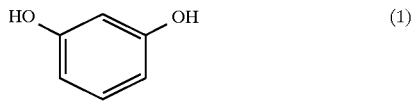

to give a diacylated compound of the formula (2)

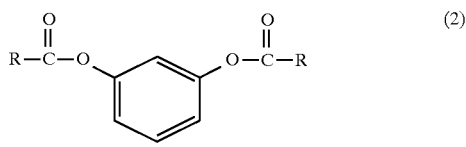

wherein R is an alkyl or phenyl group. Where R is an alkyl group, it preferably contains 1 to 3 carbon atoms and methyl is most preferred.

The acylation is preferably carried out using such an acylating agent as the acid anhydride or chloride of a carboxylic acid containing 1 to 3 carbon atoms, or benzoyl chloride. From the industrial viewpoint, the most preferred acylating agent is acetic anhydride.

The acylating agent (preferably acetic anhydride) is used in an amount of about 2 to 5 moles or more per mole of resorcinol. A preferred range is 2 to 2.5 moles.

When acetic anhydride is used as the acylating agent, the byproduct acid can serve as a solvent, hence the use of another solvent may be unnecessary. If the viscosity becomes too high during the reaction, however, the corresponding acid may be added beforehand or an organic solvent inert to the reaction may be used in an appropriate amount. When an acid chloride is used, the reaction is carried out further in the presence of a base, such as pyridine or triethylamine, which serves as a deacidifying agent.

The reaction temperature is suitably about 20° to 80° C., preferably about 30° to 70° C.

Step B

Step B is the step of subjecting the diacylated compound to Fries rearrangement to give a 4,6-diacylresorcinol of the formula (3)

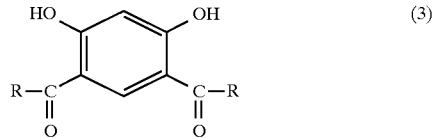

wherein R is as defined above.

This rearrangement reaction can be carried out immediately after step A or simultaneously with step A. Anyway, it is advantageous to carry out the reactions of steps A and B in one pot without isolating the diacylated compound of step A.

The Fries rearrangement reaction in step B is carried out in the presence of a Lewis acid catalyst such as zinc chloride, aluminum chloride or iron chloride. The Lewis acid is generally used in an amount of about 2 to 5 moles, preferably 2 to 2.5 moles, per mole of the diacyl compound (or resorcinol). By this reaction, the two acyl groups can be transferred to positions 4 and 6 with high site selectivity.

The reaction temperature is suitably about 120° to 180° C., optimally about 140° to 170° C. When the temperature is too low, a long reaction time is required. When the temperature is excessively high, the reaction mixture becomes highly colored, hence the reaction must be completed within a short period of time. As a result, an operability problem arises.

While the reaction can be carried out without using any solvent, those solvents inert to the reaction and suited for use in the Friedel-Crafts reaction, for example nitromethane, nitrobenzene and o-dichlorobenzene, may be used. When a solvent is used, it is generally used in an amount, on the weight basis, up to about 10 times, preferably up to about 3 times, the amount of resorcinol or the diacyl derivative thereof.

After completion of the reaction, water is added to the system to decompose the Lewis acid and the unreacted acid anhydride or acid chloride. The mixture was then diluted with a poor solvent to cause precipitation of crystals. Water may be used as the poor solvent but, when water is used, the crystals become highly colored and recrystallization becomes necessary. Therefore, water is not very suited. The most suitable poor solvent is methanol, hence the use thereof is recommended. After addition of methanol, the whole mixture is heated under reflux for promoting crystal growth and thereby facilitating solid-liquid separation.

Step C

Step C is the step of oximating the 4,6-diacylresorcinol obtained in step B to give the corresponding dioxime of the formula (4)

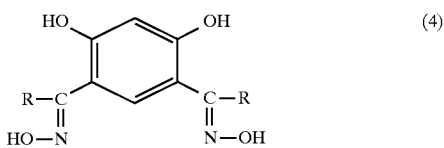

wherein R is as defined above.

The conversion of the 4,6-diacylresorcinol to the dioxime can be carried out in the conventional manner, giving an nearly quantitative yield. Thus, the 4,6-diacylresorcinol and 1.5 to 3 moles (preferably 1.9 to 2.5 moles), per mole of the 4,6-diacylresorcinol, of hydroxylamine hydrochloride are added to an amount of water which is equal to about 20 times, preferably 2 to 10 times, the amount of the 4,6-diacylresorcinol, and an aqueous alkaline solution is added dropwise at 30° to 70° C., preferably 40° to 60° C. The alkali in said aqueous alkaline solution may be the hydroxide or carbonate of an alkali or alkaline earth metal, for example sodium hydroxide, potassium hydroxide, calcium hydroxide, sodium carbonate or potassium carbonate. After completion of the addition of said aqueous alkali solution and after confirmation of the disappearance of the starting material, the reaction mixture is cooled. If necessary, the degree of coloration may be reduced by treatment with activated carbon.

After cooling, an acid is added dropwise at 0° to 40° C., preferably 15° to 30° C. The acid is, for example, sulfuric acid or hydrochloric acid. The dropping is performed until the reaction system becomes pH 7 or below, preferably pH 7 to 4. The dropping immediately causes precipitation of fine dioxime crystals.

Step D

Step D is the step of subjecting the dioxime obtained in step C to Beckmann rearrangement to give the corresponding 4,6-diacylaminoresorcinol of the formula (5)

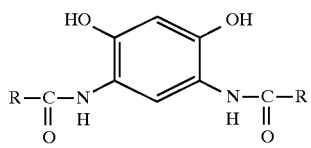

(5)

wherein R is as defined above.

The rearrangement reaction causes rearrangement in the dioxime moieties and is carried out in the presence of a rearrangement catalyst such as a protic acid or Lewis acid. The rearrangement catalyst is, for example, sulfuric acid, polyphosphoric acid, polyphosphoric acid-acetic anhydride, formic acid or boron trifluoride. The rearrangement catalyst is suitably used in an amount of about 0.01 to 100 moles per mole of the dioxime.

Organic solvents which do not adversely affect the reaction may be used as the reaction solvent. The rearrangement catalyst may serve also as the solvent.

In most cases, the reaction temperature is about 20° to 150° C., preferably about 60° to 120° C.

At the end of the reaction period, the rearrangement is driven to completion by adding water in an amount of about 1 to 100 moles per mole of the product and the 4,6-diacylaminoresorcinol is isolated by filtration or concentration. It is industrially advantageous, however, to avoid such isolation and conduct step D (Beckmann rearrangement from (4) to (5)) and step E (hydrolysis of (5) to (6)), which is to be mentioned next, in one pot. In this case, the antioxidant mentioned later can be added in the initial or middle stage of the reation.

Step E

Step E is the step of hydrolyzing the 4,6-diacylaminoresorcinol obtained in step D to give 4,6-diaminoresorcinol of the formula (6)

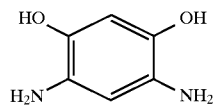

(6)

or a salt thereof.

The hydrolysis can be achieved with ease, typically by adding hydrochloric acid in an amount of 2 to 10 moles per mole of the reaction product of step D (4,6-diacylaminoresorcinol) and an antioxidant, for example stannous chloride, in an amount of 0.01 to 0.5 mole on the same basis and heating the resulting mixture at about 50° to 120° C., whereby 4,6-diaminoresorcinol or a salt thereof can be obtained.

4,6-Diaminoresorcinol generally precipitates out in the form of dihydrochloride crystals. The crystals are collected and, when necessary, purified in the conventional manner.

The steps involved in the process of the present invention may be summarized as shown below in Table 1.

TABLE 1

| Compound (formula) | Step | Reaction |
| --- | --- | --- |
| Resorcinol (1) | | |
| ↓ | A | Acylation |
| Diacyl compound (2) | | |
| ↓ | B | Fries rearrangement |
| 4,6-Diacylresorcinol (3) | | |
| ↓ | C | Oximation |
| Dioxime (4) | | |
| ↓ | D | Beckmann rearrangement |
| 4,6-Diacylaminoresorcinol (5) | | |

TABLE 1-continued

| Compound (formula) | Step | Reaction |
| --- | --- | --- |
| ↓ | E | Hydrolysis |
| 4,6-Diaminoresorcinol (6) or a salt thereof | | |

The above series of reactions does not involve any nitro compound or halogen compound tending to cause byproduct formation. In each step of substituent introduction, the regioselectivity is high and the yield in each step is high (in step C and step E, in particular, nearly quantitative). Furthermore, step A and step B can be performed in one pot and step D and step E as well can be performed in one pot.

The following examples are further illustrative of the present invention.

EXAMPLE 1

Synthesis of 4,6-diacetylresorcinol/Steps A and B

Resorcinol (20.0 g, 0.1816 mole) was dissolved in 42.65 g (0.4178 mole) of acetic anhydride, 63.16 g (0.4644 mole) of zinc chloride was added and the mixture was heated. After 3 hours of heating of the mixture at 150° to 160° C., 4,6-diacetylresorcinol crystallized out. After cooling, 25 g of water was added for hydrolyzing the remaining acetic anhydride, then 40 g of methanol was added and, for growing crystals, the resulting mixture was heated under reflux for 30 minutes, then cooled, and subjected to solid-liquid separation. The solid was washed with 168 g of methanol and then dried, whereby 26.03 g (0.1340 mole) of 4,6-diacetylresorcinol was obtained. The yield was 73.8% on the resorcinol basis. The thus-obtained 4,6-diacetylresorcinol had the following physical characteristics.

Melting point: 178° to 180° C.

IR (KBr, cm$^{-1}$): 3700–2200, 1660, 1640, 1590, 1490, 1370, 1320, 1260

$^1$H-NMR (270 MHz, in $d_6$-DMSO): δ=2.65 (6H, s, $CH_3$×2), 6.37, 8.40 (1H×2, s, aromatic H×2), 12.7 (2H, br, OH)

$^{13}$C-NMR (68 MHz, in $d_6$-DMSO): δ=27.19, 103.34, 114.07, 137.32, 166.94, 202.59

Dioxime Synthesis/Step C

To a mixture of 23.55 g (0.1212 mole) of the above product, namely 4,6-diacetylresorcinol, 196 g of water and 70.76 g of 48% caustic soda was added 20.11 g (0.2910 mole) of hydroxylamine hydrochloride, and the reaction was allowed to proceed at 55° C. for 30 minutes. After cooling, the reaction mixture was subjected to activated carbon treatment, 91.12 g of concentrated hydrochloric acid was added dropwise to the filtrate, and the crystalline precipitate dioxime was separated by solid-liquid separation, washed with water and dried to give 26.22 g (0.1169 mole) of the dioxime. The yield was 96.5% on the 4,6-diacetylresorcinol basis. The dioxime obtained had the following characteristic values.

IR (KBr, cm$^{-1}$): 3600–2000, 1625, 1612, 1495, 1360, 1310, 1260, 1240

$^1$H-NMR (270 MHz, in $d_6$-DMSO): δ=2.28 (6H, s, $CH_3$×2), 6.34, 7.48 (1H×2, s, aromatic H×2), 11.3 (2H, s, NOH×2), 12.0 (2H, br, OH×2)

$^{13}$C-NMR (68 MHz, in $d_6$-DMSO): δ=10.86, 103.56, 111.63, 127.57, 157.14, 159.28

Synthesis of 4,6-diaminoresorcinol dihydrochloride/Steps D and E

A mixture of 5.12 g (0.02283 mole) of the dioxime obtained as mentioned above and 27.53 g of polyphosphoric acid was heated at 90° to 100° C. for 1.5 hours. After cooling, 0.53 g of stannous chloride, 10 g of water and 15 ml of concentrated hydrochloric acid were added, and the mixture was heated at 95° C. for 4 hours, whereupon white crystals of 4,6-diaminoresorcinol dihydrochloride precipitated out. After cooling and solid-liquid separation, the solid obtained was washed with concentrated hydrochloric acid and then with acetone and dried to give 3.80 g (0.01784 mole) of 4,6-diaminoresorcinol dihydrochloride. The yield was 78.1% on the dioxime basis. The thus-obtained 4,6-diaminoresorcinol dihydrochloride had the following characteristic values.

IR (KBr, cm$^{-1}$): 3700–2000, 1650, 1635, 1570, 1550, 1505, 1490, 1370, 1210

$^1$H-NMR (400 MHz, in $D_2O$ with $SnCl_2$/HCl added): δ=6.78, 7.45 (1H×2, s, aromatic H×2)

$^{13}$C-NMR (100 MHz, in $D_2O$ with $SnCl_2$/HCl added): δ=106.78, 112.50, 122.40, 154.20

EXAMPLE 2
Synthesis of 4,6-diaminoresorcinol dihydrochloride/Steps D and E

The steps D and E of Example 1 were modified as follows. A mixture of 1.06 g (0.00473 mole) of the dioxime and 10 ml of formic acid was heated under reflux for 1.5 hours. Thereafter, the formic acid was distilled off under reduced pressure, 2 ml of a 5% (by weight) aqueous solution of stannous chloride and 3 ml of concentrated hydrochloric acid were added to the residue and the mixture was heated at 70° to 90° C. for 1 hour, whereupon crystals precipitated out. After cooling and solid-liquid separation, the solid was washed with concentrated hydrochloric acid and then with acetone and dried to give 0.648 g (0.00304 mole) of crystals. The yield was 64% on the dioxime basis. Based on the results of IR analysis, these crystals could be identified as 4,6-diaminoresorcinol dihydrochloride.

EXAMPLE 3
Synthesis of 4,6-diaminoresorcinol dihydrochloride/Steps D and E

The steps D and E of Example 1 were modified as follows. A mixture of 0.43 g (0.0019 mole) of the dioxime and 3 ml of concentrated sulfuric acid was heated at 60° to 80° C. for 1.5 hours. Thereafter, the reaction mixture was added dropwise to 10 ml of a 5% (by weight) aqueous solution of stannous chloride, then 5 ml of concentrated hydrochloric acid was added, and the mixture was heated at 75° to 80° C. for 2 hours, whereupon crystals precipitated out. After cooling and solid-liquid separation, the solid was washed with concentrated hydrochloric acid and then with acetone and dried to give 0.22 g (0.0010 mole) of crystals. The yield was 53% on the dioxime basis. Based on the results of IR analysis, these crystals could be identified as 4,6-diaminoresorcinol dihydrochloride.

EXAMPLE 4
Synthesis of 4,6-diaminoresorcinol dihydrochloride/Steps D and E

The steps D and E of Example 1 were modified as follows. A mixture of 2.95 g of Polyphosphoric acid, 19.29 g of acetic anhydride and 10.0lg of the dioxime was heated at 90° to 100° C. for about 3 hours. After cooling, to the reaction mixture were added 1.56 g of stannous chloride, 25 g of water and 32 g of concentrated hydrochloric acid, and the mixture was heated at 90° to 110° C. for 5 hours, whereupon crystals precipitated out. After cooling and solid-liquid separation, the solid was washed with 17.5% (by weight) aqueous solution of hydrochloric acid and then with acetone and dried to give 5.61 g of crystals. The yield was 59.3% on the dioxime basis. Based on the results of IR analysis, these crystals could be identified as 4,6-diaminoresorcinol dihydrochloride.

EFFECTS OF THE INVENTION

According to the present invention, the desired product 4,6-diaminoresorcinols can be produced in an industrially advantageous manner without involving any nitro compound or halogen compound but in high yields and with high regioselectivity in each step of substituent introduction.

What is claimed is:

1. A process for producing 4,6-diaminoresorcinols which comprises the steps of:

subjecting a dioxime of the formula (4)

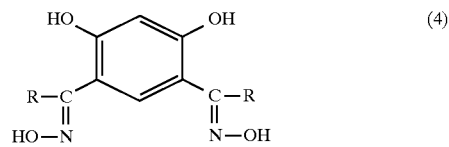

wherein R is an alkyl or phenyl group, to Beckmann rearrangement to thereby produce 4,6-diacylaminoresorcinol of the formula (5)

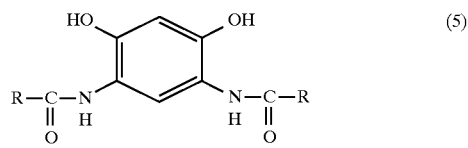

wherein R is as defined above, and subjecting said 4,6-diacylaminoresorcinol to hydrolysis and recovering the product 4,6-diaminoresorcinol of the formula (6)

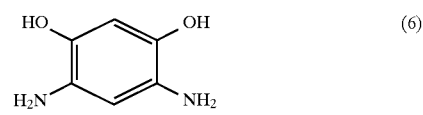

or a salt thereof.

2. A process as claimed in claim 1, wherein the Beckmann reaction from (4) to (5) and the hydrolysis reaction from (5) to (6) are carried out in one pot.

3. A process as claimed in claim 1, wherein the Beckmann reaction from (4) to (5) is carried out in formic acid, polyphosphoric acid, sulfuric acid or polyphosphoric acid-acetic anhydride.

4. A process as claimed in claim 1, wherein the hydrolysis reaction from (5) to (6) is carried out using hydrochloric acid.

5. A process as claimed in claim 2 or 4, wherein the reaction from (4) to (6) via (5) or the reaction from (5) to (6) is carried out in the presence of an antioxidant.

6. A process as claimed in claim 5, wherein the antioxidant is stannous chloride.

7. A process as claimed in claim 1 wherein the dioxime of formula (4) is prepared by acylating resorcinol of the formula (1)

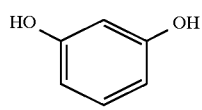
(1)
and subjecting the resulting diacylated compound of the formula (2)
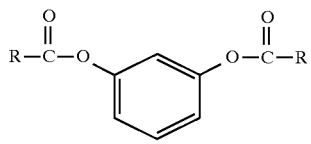
(2)
alkyl or phenyl group, to Fries rearrangement and further oximating the resulting 4,6-diacylresorcinol of the formula (3)
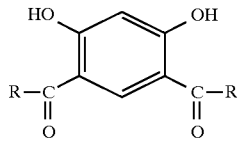
(3)
wherein R is as defined above.
* * * * *